United States Patent [19]

Heine et al.

[11] Patent Number: 4,654,220
[45] Date of Patent: Mar. 31, 1987

[54] PARTING OILS FOR BAKED GOODS AND METHOD OF PREPARATION

[75] Inventors: Christian Heine, Monheim; Reinhold Wuest, Kaarst, both of Fed. Rep. of Germany

[73] Assignee: Henkel Kommanditgesellschaft auf Aktien, Duesseldorf, Fed. Rep. of Germany

[21] Appl. No.: 848,653

[22] Filed: Apr. 7, 1986

Related U.S. Application Data

[62] Division of Ser. No. 663,018, Oct. 19, 1984, Pat. No. 4,605,563.

[30] Foreign Application Priority Data

Nov. 10, 1983 [DE] Fed. Rep. of Germany ....... 3340680

[51] Int. Cl.$^4$ ............................................... A23D 5/00
[52] U.S. Cl. .................................... 426/609; 426/612; 426/811
[58] Field of Search .................. 426/609, 612, 811

[56]  References Cited

U.S. PATENT DOCUMENTS 3,360,376 12/1967 Dobson ........................... 426/601 X
3,397,997 8/1968 Japiske .......................... 426/601 X
4,375,483 3/1983 Shuford et al. ................ 426/606 X

FOREIGN PATENT DOCUMENTS 979730 12/1975 Canada ................................ 426/601

OTHER PUBLICATIONS

Hawley, G. G., "The Condensed Chemical Dictionary", Van Nostrand Reinhold Co., N.Y., 1981, p. 920.

Primary Examiner—Robert Yoncoskie
Attorney, Agent, or Firm—Ernest G. Szoke; Henry E. Millson, Jr.

[57]  ABSTRACT

A synergistic effect on the viscosity behavior of oils is obtained by the addition of a combination of from 0.1% to 10% by weight of a high-melting glyceride of saturated fatty acids ($C_{14}$–$C_{24}$) melting above 50° C. (A) and from 0.2% to 10% by weight of a highly dispersed, pyrogenic silica (B), the weight ratio of (A) to (B) amounting to between 20:80 and 80:20. A distinct increase in viscosity may be obtained with relatively small additions of from 0.1% to 1.0% by weight of (A) and from 0.2% to 2% by weight of (B); additions of 1% by weight of (A) and 2% by weight of (B) in a ratio by weight of (A) to (B) of from 25:75 to 50:50 are required to obtain a pasty consistency. Liquid unsaturated triglyceride oils and/or unsaturated fatty acid esters of higher fatty alcohols containing said high-melting glycerides and pyrogenic silica have utility as parting oils for baked goods.

5 Claims, No Drawings

PARTING OILS FOR BAKED GOODS AND METHOD OF PREPARATION

This application is a division of Ser. No. 663,018, filed Oct. 19, 1984 now U.S. Pat. No. 4,605,563.

BACKGROUND OF THE INVENTION

It is known that the viscosity of oils can be increased by additions of finely divided solids. Highly dispersed silica is particularly suitable for that purpose. On the other hand, additions of high-melting fats, for example, hardened glycerides of relatively long chain length, have the same effect.

In addition, additions of the above-mentioned substances may occasionally produce thixotropy phenomena. This means that the oils reduce their viscosity under shear stressing, but change back to their relatively high viscosity state after standing.

A significant synergistic effect on the viscosity behavior of oils has now surprisingly been found whereby highly dispersed silica and high-melting fats intensify one another's effectiveness to an unexpectedly high degree.

OBJECTS OF THE INVENTION

An object of the present invention is to develop a process for increasing the viscosity of oils by adding thereto a synergistically acting mixture of highly dispersed silica and high melting fats.

Another object of the present invention is the development of a process for increasing the viscosity of, or thickening, oils comprising adding to a low viscosity oil (A) from 0.1% to 10% by weight, based on the final composition, of a high-melting glyceride of saturated fatty acids having a chain length of from $C_{14}$ to $C_{24}$ and a melting point of above 50° C., and (B) from 0.2% to 10% by weight, based on the final composition, of a highly dispersed, pyrogenic silica having submicron particles, where the weight ratio of (A) to (B) is between 20:80 and 80:20.

These and other objects will become more apparent as the description thereof proceeds.

DESCRIPTION OF THE INVENTION

Accordingly, the present invention relates to a process for increasing the viscosity of, i.e., thickening, oils which is characterized in that from 0.1% to 10% by weight of a high-melting glyceride of saturated $C_{14}$–$C_{24}$ fatty acids melting above 50° C. (A) and from 0.2% to 10% by weight of a highly disperse silica (B), the ratio of (A) to (B) amounting to between 20:80 and 80:20, are added to the oils in a total quantity of from 0.3% to 20% by weight, the percentages being based on the mixture as a whole, i.e., on the thickened oil.

More particularly, the present invention relates to a process for increasing the viscosity of, or thickening, oils comprising adding to a low viscosity oil (A) from 0.1% to 10% by weight, based on the final composition of a high-melting glyceride of saturated fatty acids having a chain length of from $C_{14}$ to $C_{24}$ and a melting point of above 50° C., and (B) from 0.2% to 10% by weight, based on the final composition, of a highly dispersed, pyrogenic silica having submicron particles, where the weight ratio of (A) to (B) is between 20:80 and 80:20.

In the context of the invention, "oils" are understood to be water-insoluble organic compounds of low vapor pressure which are liquid at room temperature and of which the common feature is their oil-like physical consistency. The oils have a viscosity of at least 40 mPa.s and a molecular weight of at least 140. Particularly appropriate liquids of this type are, above all, natural or synthetic glycerides of higher fatty acids having chain lengths of from $C_6$ to $C_{24}$, the $C_{12}$–$C_{24}$ fatty acids of which containing one or more double bonds. Mention may also be made of higher fatty acids or fatty alcohols having chain lengths of from $C_6$ to $C_{24}$ and esters and ethers thereof, providing they have an oil-like consistency, and also of mineral oils.

Suitable high-melting fatty acid glycerides (A) are the mono-, di- and - in particular - triglycerides of palmitic, stearic, hydroxystearic and behenic acid, optionally with proportions of higher fatty acids (up to $C_{24}$), which acids and mixtures of acids have melting points in the range from 50° C. to 90° C. Examples thereof are hardened vegetable or animal oils, such as hardened castor oil, tallow, lard, palm oil and also glycerol monostearate or glycerol monobehenate.

Suitable highly dispersed, pyrogenic silica having submicron particles "B" are those silicas exposed to temperatures of 1100° C. or higher, which have a high surface area. Examples of such highly dispersed silicas are those sold by the firm Degussa A.G. of Frankfurt, Federal Republic of Germany, under the trademark Aerosil ®.

The process according to the invention for increasing viscosity is of considerable commercial significance for numerous applications:

For example, cosmetic and pharmaceutical oils based on physiologically compatible liquid oil components may have their viscosity increased as required. Compatible liquid oil components of the type in question are, for example, vegetable and animal oils, for example, triglycerides and fatty alcohol esters based on fatty acids containing a relatively high proportion of unsaturated $C_{12}$–$C_{22}$ fatty acids, above all oleic acid, linoleic acid, erucic acid, for example, olive oil, rape oil, palm oil, soyabean oil, sperm oil. Other suitable cosmetic-pharmaceutical oil components are liquid, medium-chain fatty acid triglycerides of $C_8$–$C_{10}$-fatty acids, $C_{12}$–$C_{22}$ fatty acid esters of higher fatty alcohols, such as for example oleyl oleate, $C_{12}$–$C_{22}$ fatty acid esters of lower alkanols such, for example, isopropyl myristate, $C_{12}$–$C_{22}$ fatty acid esters of branched-chain alkanols, such as, for example, 2-ethylhexyl stearate, 2-hexyldecyl palmitate, liquid unsaturated fatty alcohols such as, for example, oleyl alcohol, branched $C_{12}$–$C_{36}$ alkanols such as, for example, 2-hexyldecanol, 2-octyldodecanol, and finally also $C_{12}$–$C_{22}$ fatty alcohol poly-lower alkyleneglycol ethers, for example, the adduct of 15 mols of ethylene oxide onto oleyl alcohol, or the adduct of 10 mols of ethylene oxide and 20 mols of propylene oxide onto cetyl/stearyl alcohol, $C_{12}$–$C_{22}$ fatty acid poly-lower alkyleneglycol esters, $C_{12}$–$C_{22}$ fatty acid esters of ethylene oxide and propylene oxide adducts onto fatty alcohols, lower alkylene glycols or glycerol and also liquid paraffin oils.

Another application for the process according to the invention is in the field of edible oils, carrier oils for food additives, for example for slices, and parting oils for baked goods and confectionery. Edible oils and carrier oils for spices and flavorings are based on liquid vegetable and animal fatty acid triglyceride oils, for example, soyabean oil, sunflower oil, rape oil, olive oil, palm oil, coconut oil and mixtures of these and other known food-grade oils. Oil-like mono- and diglycerides, for example, glycerol monooleate and glycerol dioleate, which may be used as emulsifiers in the food industry, may also be thickened by the process according to the invention.

Parting oils for baked goods and confectionery may also be thickened by the process according to the invention. In this case, relatively small additions of from 0.1% to 1% by weight of high-melting triglyceride (A) and from 0.2% to 2.0% by weight of highly dispersed silica (B) are sufficient to produce a considerable increase in adhesion to metal surfaces, particularly at high temperatures. Suitable liquid oils are, for example liquid unsaturated triglycerides, such as the natural vegetable and animal oils suitable as edible oils, synthetic unsaturated fatty acid triglycerides and liquid, unsaturated fatty acid esters of higher fatty alcohols, such as, for example, sperm oil filtrate, cetyl oleate, oleyl oleate, oleyl palmitate and mixtures of those oils. The oils thickened by the process according to the invention may readily be applied to the baking pans, for example by means of spray guns, without clogging the fine jets.

Lubricants based on liquid mineral oils and/or liquid synthetic ester oils may be thickened as required by the process according to the invention up to the consistency of lubricating grease. Suitable synthetic ester oils are, for example, the esters of polyhydric alcohols, such as the polyhydric alkanols, pentaerythritol, neopentyl glycol, trimethylol propane, glycerol, with linear or branched alkane carboxylic acids, preferably containing from 5 to 15 C-atoms, the esters of alkane dicarboxylic acids and benzene dicarboxylic acids, such as adipic acid, azelaic acid, sebacic acid, phthalic acid, with saturated, linear or branched alkanols, preferably containing from 4 to 12 C-atoms, complex esters of polyhydric alkanols, alkane carboxylic acids and dicarboxylic acids of the abovementioned type and also fatty acid polylower alkyleneglycol esters and triethanolamine fatty acid esters.

A significant increase in the viscosity of the oils may be obtained even with relatively small additions of from 0.1% to 1% by weight of (A) and from 0.2% to 2% by weight of (B), depending on the type of oil involved. Additions of at least 1.0% by weight of (A) and 2% by weight of (B), in all about 3% to 10.0% by weight of (A) and (B), are generally required for obtaining paste-like consistencies. More specifically, however the necessary additions depend upon the physical and chemical properties of components (A) and (B) and upon those of the oils to be thickened.

Components (A) and (B) may be individually added to the oils in any order. The ratio of (A) to (B) preferably amounts to between 25:75 and 50:50 by weight. It is best initially to add the fatty acid glyceride (A) to the heated oil with intensive stirring and then the silica (B) and, thereafter, to cool the mixture rapidly to room temperature with continued intensive stirring.

To produce only slightly thickened oils, in whose case it is more important to obtain an improvement in adhesiveness or in dispersibility and in their ability to carry additives rather than to increase viscosity, it is advisable initially to prepare a relatively high-viscosity to paste-like concentrate of the high-melting triglyceride (A) and the highly dispersed silica (B) in the oil, of which the viscosity, adhesiveness and ability to carry additives are to be increased, and then further to dilute the concentrate thus prepared with the liquid oil. A concentrate such as this preferably contains from 1% to 10% by weight of the high-melting triglyceride and from 2% to 10% by weight of the highly dispersed silica.

To produce a parting oil for baked goods, a concentrate of the type in question would be prepared from one of the above-mentioned liquid oils suitable for bakery parting oils. The product suitable for use as a bakery parting oil is prepared from the concentrate by diluting the concentrate with more liquid oil in the absence of heat until the content of high-melting triglyceride (A) is in the range from 0.1% to 1% by weight and the content of highly dispersed silica (B) in the range from 0.2% to 2% by weight, based on the final parting oil.

It is possible by the measure according to the invention to obtain an extraordinary increase in viscosity in a variety of different oils which could not be obtained with the same quantity of one of the individual components. It is even possible to obtain gel-like or paste-like consistencies which, by virtue of their thixotropic properties, may readily be liquified by stirring or the like which can be of considerable significance so far as convenient handling and use of the products are concerned.

In addition, the oils thickened in accordance with the invention show improved adhesion to solid surfaces, particularly at elevated temperatures, and an improved dispersibility and ability to carry dispersed additives.

The following Examples are intended to illustrate the invention without limiting it in any way.

EXAMPLE 1

The following Table shows the increase in viscosity of rape oil and mineral oil by the addition of a total of 6% by weight of various high-melting fatty acid glycerides (A) and Aerosil 200 ® (B) in various quantitative ratios. The synergistic effect of the combinations of (A) and (B) is clearly apparent.

Viscosity was measured by means of a Brookfield RVT viscosimeter at 20° C./20 r.p.m.

Aerosil 200 ® is a highly dispersed, pyrogenic silica having submicron particles.

| Viscosity Increase of Oils | | | | | | | | | |
|---|---|---|---|---|---|---|---|---|---|
| Oil type | Rape oil | | | | | | | | |
| Test No. | a | b | c | d | e | f | g | h | i |
| Additions in % | | | | | | | | | |
| highly disperse silica (Aerosil 200 ®) | 0 | 6 | 4.5 | 3.9 | 3.6 | 3 | 1.5 | 0 | 3.9 |
| Hardened castor oil | | | 1.5 | 2.1 | 2.4 | 3 | 4.5 | 6 | |
| Hardened tallow | | | | | | | | | 2.1 |
| Hardened lard | | | | | | | | | |
| Hardened palm oil | | | | | | | | | |
| Glycerol mono- | | | | | | | | | |

-continued

Viscosity Increase of Oils

| Stearate Glycerol mono-behenate | | | | | | | | | |
|---|---|---|---|---|---|---|---|---|---|
| Viscosity mPa·s* | 100 | 3900 | 26500 | 28500 | 26000 | 22000 | 4400 | 1300 | 26500 |
| Consistency | lq | tc-lq | past. | past. | past. | past. | tc-lq | lq | past. |

| Oil type | Rape oil | | | | Mineral oil | | |
|---|---|---|---|---|---|---|---|
| Test No. | j | k | l | m | n | o | p |
| Additions in % | | | | | | | |
| highly disperse silica (Aerosil 200 ®) | 3.9 | 3.9 | 3.9 | 3.9 | 0 | 6 | 3.9 |
| Hardened castor oil | | | | | | | |
| Hardened tallow | | | | | | | |
| Hardened lard | 2.1 | | | | | | |
| Hardened palm oil | | 2.1 | | | | | 2.1 |
| Glycerol mono-Stearate | | | 2.1 | | | | |
| Glycerol mono-behenate | | | | 2.1 | | | |
| Viscosity mPa·s* | 25000 | 52000 | 11000 | 34000 | 400 | 16000 | 66000 |
| Consistency | past. | past. | tn-lq | past. | lq | past. | past. |

*Brookfield viscosimeter, type RVT, 20° C./20 r.p.m.
lq = liquid
tc-lq = thickly liquid
past. = pasty
tn-lq = thinly liquid

EXAMPLE 2

(a) Edible oil, pasty 1000 g of rape oil having a viscosity of 100 mPa.s were heated to 90° C. and 21 g of melted, hardened castor oil (M.p. 84° C.) and 39 g of Aerosil 200 ® were introduced with stirring. The mixture was indirectly cooled with ice water to 20° C. with intensive stirring. After storage for 24 hours at room temperature, the oil had a paste-like consistency with a viscosity of 26,000 mPa.s, as measured with a Brookfield RVT viscosimeter at 20° C./20 r.p.m.

(b) Edible oil, thickly liquid

As in Example 2a, 10.5 g of melted, hardened castor oil (M.p. 84° C.) and 19.5 g of Aerosil 200 ® were introduced into 1000 g of rape oil. After storage for 24 hours at room temperature, the oil had a thickly liquid consistency and a viscosity of 7500 mPa.s.

(c) Edible oil, liquid

As in Example 2a, 2.1 g of melted, hardened castor oil (M.p. 84° C.) and 3.9 g of Aerosil 200 ® were introduced into 1000 g of rape oil. After storage for 24 hours at room temperature, the oil had an increased viscosity of 360 mPa.s.

EXAMPLE 3

(a) Mineral oil product, pasty 1000 g of mineral oil were introduced into a stirrer-equipped vessel with 21 g of hardened palm oil (M.p. 55° C.) and 39 g of Aerosil 200 ®, followed by heating to 90° C. After the products had dissolved, the solution was rapidly cooled to 20° C. with intensive stirring.

After storage for 24 hours at room temperature, the oil had a paste-like consistency with a viscosity (measured in the same way as in Example 1) of 66,000 mPa.s. The starting mineral oil had a viscosity of 400 mPa.s.

(b) Mineral oil product, thickly liquid

As in Example 3a, 7.0 g of hardened palm oil and 13.0 g of Aerosil 200 ® were introduced into 1000 g of mineral oil. After storage for 24 hours at room temperature, the oil had a thickly liquid consistency and a viscosity of 12,800 mPa.s.

EXAMPLE 4

(a) Skin function oil containing animal tissue or organ extract, pasty 855 g of a mixture of higher unsaturated $C_{16}$–$C_{18}$ alcohol, $C_{12}$–$C_{14}$ fatty acid isopropyl ester and medium-chain $C_8$–$C_{10}$ fatty acid triglyceride were introduced into a stirrer-equipped vessel. 25 g of hardened castor oil and 45 g of Aerosil 200 ® were then introduced into the mixture, followed by heating to 90° C. until a clear oily solution had formed. The solution formed was then rapidly cooled to 20° C. with intensive stirring and 5 g of soluble native collagen and 25 g of wheat germ oil were introduced into the mixture.

After storage for 24 hours at room temperature, the skin function oil had a paste-like consistency and a viscosity (measured as in Example 1) of 10,500 mPa.s.

Without the addition of hardened castor oil and Aerosil ®, the skin function oil was thinly liquid with a viscosity of only 50 mPa.s.

(b) Skin function oil containing animal tissue or organ extract, thickly liquid As in Example 4a, 14 g of hardened castor oil and 26 g of Aerosil 200 ®, 5 g of animal tissue or organ extract and 25 g of wheat germ oil were introduced into 855 g of a mixture of higher unsaturated $C_{16}$–$C_{18}$ alcohol, $C_{12}$–$C_{14}$ fatty acid isopropyl ester and medium-chain $C_8$–$C_{10}$ fatty acid triglyceride.

After storage for 24 hours at room temperature, the skin function oil had a thickly liquid consistency and a viscosity of 2500 mPa.s.

EXAMPLE 5

(a) Re-moisturizing bath oil, pasty 830 g of oleyl alcohol polyethyleneglycol ether (7 EO) were introduced into a stirrer-equipped vessel. 25 g of castor oil (hardened) and 45 g of Aerosil 200 ® were then added with stirring. The mixture was heated to 90° C. and, after the products had dissolved, the solution was rapidly cooled to 20° C. with intensive stirring. Finally, 100 g of a perfume concentrate were added with stirring.

After storage for 24 hours at room temperature, the bath oil had a pasty consistency and a viscosity (measured as in Example 1) of 72,000 mPa.s.

Without the addition of hardened castor oil and Aerosil ®, the bath oil was thinly liquid and had a viscosity of only 100 mPa.s.

(b) Re-moisturizing bath oil, thickly liquid

As in Example 5a, 17.5 g of hardened castor oil and 32.5 of Aerosil 200 ® together with 100 g of perfume concentrate were introduced into 830 g of oleyl alcohol polyethyleneglycol ether (7 EO).

After storage for 24 hours at room temperature, the bath oil had a thickly liquid consistency and a viscosity of 7900 mPa.s.

EXAMPLE 6

Cosmetic oil 1000 g of decyl oleate or oleyl oleate or a mixture of both were heated to 90° C., followed by the introduction with stirring of 21 g of melted hardened castor oil (M.p. 84° C.) and 39 g of Aerosil 200 ®. The mixture was indirectly cooled with ice water to 20° C. with intensive stirring.

After storage for 24 hours at room temperature, the oil had a pasty consistency and a viscosity of 32,000 mPa.s (measured as in Example 1).

The starting produce was thinly liquid and had a viscosity of 95 mPa.s.

EXAMPLE 7

(a) Edible oil, pasty 1000 g of soyabean, oil were heated to 90° C., followed by the introduction with stirring of 26 g of melted, hardened lard and 49 g of Aerosil 200 ®. The mixture was indirectly cooled with ice water to 20° C. with intensive stirring.

After storage for 24 hours at room temperature, the oil had a pasty consistency and a viscosity of 29,000 mPa.s (measured as in Example 1).

EXAMPLE 8

(a) Edible oil, pasty 1000 g of olive oil were heated to 90° C., followed by the introduction with stirring of 21 g of melted glycerol monostearate (M.p. 67° C.) and 39 g of Aerosil 200 ®. The mixture was indirectly cooled with ice water to 20° C. with intensive stirring.

After storage for 24 hours at room temperature, the oil had a pasty consistency and a viscosity of 18,000 mPa.s (measured as in Example 1).

EXAMPLE 9

(a) Edible oil, pasty 1000 g of sunflower oil were heated to 90° C., followed by the introduction with stirring of 26 g of melted, hardened palm oil (M.p. 55° C.) and 49 g of Aerosil 200 ®. The mixture was indirectly cooled with ice water to 20° C. with intensive stirring.

After storage for 24 hours at room temperature, the oil had a pasty consistency and a viscosity of 28,000 mPa.s (measured as in Example 1).

EXAMPLE 10

Bakery parting oil

A mixture of 90.0 g of soyabean oil (refined) and 4.0 g of soya lecithin, 2.1 g of hardened palm oil and 3.9 g of Aerosil 200 ® was heated with stirring to 90° C.

The mixture was indirectly cooled with ice water to 20° C. while stirring. It was then added with stirring to 900 g of refined soyabean oil until a homogeneous mixture was obtained. A liquid bakery parting oil with a viscosity of 148 mPa.s at 20° C. was obtained.

Without the addition of hardened palm oil and Aerosil 200 ®, the mixture as a whole had a viscosity of 105 mPa.s at 20° C.

The bakery parting oil was sprayed onto the baking pans by means of a spray gun.

The preceding specific embodiments are illustrative of the practice of the invention. It is to be understood, however, that other expedients known to those skilled in the art or disclosed herein may be employed without departing from the spirit of the invention or the scope of the appended claims.

We claim:

1. A parting oil for baked goods with a considerable increase in adhesion to metal surfaces and improved spray properties consisting essentially of from 97% to 99.7% by weight of a liquid unsaturated triglyceride oil and/or an unsaturated fatty acid ester of higher fatty alcohols, from 0.1% to 1% by weight of a high-melting glyceride of saturated $C_{14}$–$C_{24}$ fatty acids melting above 50° C. to 90° C. selected from the group consisting of monoglyceride of palimitic acid, diglyceride of palmitic acid, triglyceride of palmitic acid, monoglyceride of stearic acid, diglyceride of stearic acid, triglyceride of stearic acid, monoglyceride of hydroxystearic acid, diglyceride of hydroxystearic acid, triglyceride of hydroxystearic acid, monoglyceride of behenic acid, diglyceride of behenic acid, triglyceride of behenic acid and mixtures thereof and from 0.2% to 2% by weight of a highly dispersed pyrogenic silica having submicron particles where the weight ratio of said high-melting glyceride to said highly dispersed silica is between 25:75 and 50:50.

2. The parting oil of claim 1, wherein said high-melting glyceride of saturated fatty acids having a chain length of from $C_{14}$–$C_{24}$ and a melting point above 50° C. to 90° C. is selected from the groups consisting of hardened vegetable or animal oils.

3. The parting oil of claim 1 wherein said hardened vegetable or animal oils are selected from the group consisting of hardened castor oil, hardened tallow, hardened lard and hardened palm oil.

4. The parting oil of claim 1 wherein said liquid unsaturated triglyceride oil and/or an unsaturated fatty acid ester of higher fatty alcohols are selected from the group consisting of liquid unsaturated natural vegetable and animal oils suitable as edible oils, synthetic unsaturated fatty acid triglycerides, sperm oil filtrate, cetyl oleate, oleyl oleate, oleyl palmitate, and mixtures thereof.

5. A process for the production of a parting oil for baked goods comprising adding to a liquid unsaturated triglyceride oil and/or an unsaturated fatty acid ester of higher fatty alcohols (A) from 0.1% to 1% by weight, based on the final composition, of a high-melting glyceride of saturated fatty acids having a chain length of from $C_{14}$ to $C_{24}$ and a melting point of above 50° C. to 90° C. selected from the group consisting of monoglyceride of palimitic acid, diglyceride of palmitic acid, triglyceride of palmitic acid, monoglyceride of stearic acid, diglyceride of stearic acid, triglyceride of stearic acid, monoglyceride of hydroxystearic acid, diglyceride of hydroxystearic acid, triglyceride of hydroxystearic acid, monoglyceride of behenic acid, diglyceride of behenic acid, triglyceride of behenic acid and mixtures thereof, and (B) from 0.2% to 2% by weight, based on the final composition, of a highly dispersed, pyrogenic silica having submicron particles, where the weight ratio of (A) to (B) is between 25:75 and 50:50, and recovering a parting oil for baked goods with a considerable increase in adhesion to metal surfaces and improved spray properties.

* * * * *